United States Patent [19]

Lehn et al.

[11] 4,085,507
[45] Apr. 25, 1978

[54] APPLIANCE FOR TAKING DENTAL IMPRESSIONS AND METHOD AND APPARATUS FOR MAKING THE SAME

[76] Inventors: F. Heinrich Lehn, Unionstrasse 5, 4760 Werl; Hans-Jürgen Schmitter, Sonnenwall 29, 4300 Duisburg, bothof, Germany

[21] Appl. No.: 704,546

[22] Filed: Jul. 12, 1976

[30] Foreign Application Priority Data

May 5, 1976 Germany .............................. 2619799

[51] Int. Cl.$^2$ .............................................. A61C 9/00
[52] U.S. Cl. ......................................................... 32/17
[58] Field of Search ............................................... 32/17

[56] References Cited

U.S. PATENT DOCUMENTS 3,736,663  6/1973  White ........................................ 32/17

Primary Examiner—Robert Peshock
Attorney, Agent, or Firm—Max Fogiel

[57] ABSTRACT

An arrangement for a dental impression appliance which has a reception channel adapted to the shape of the human jaw for receiving impression materials. The channel is horseshoe-shaped with open and closed sides. The reception channel, furthermore, is bounded on one side by a base plate and along its inner and outer edge by sections extending or turning upwards from the plane of the base plate. The sections are provided on the inside of the reception channel and have retention edges directed away from the base plate. The sections have undercuts in the area of the channel side that is open. The impression appliance is in the form of a one-piece plastic molded part with the retention edges directly molded from the sections extending from the plane of the base plate. A handgrip extends outward from the base plate on the closed side of the horseshoe shape. The shaped parts of the appliance are molded in a two-piece mold joined along a mating surface, while the parts being molded are in a substantially warm and partially plastic condition. Brief elastic deformation is applied to the areas adjacent to the undercuts. The appliance is produced by an extrusion die with tool sections joined along the mating surface and having a cavity corresponding to the impression appliance. The mating surface conforms to the retention edge which extends along the turned-up sections bounding on the outside the reception channel at a predetermined distance from the base plate.

2 Claims, 10 Drawing Figures

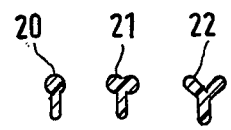
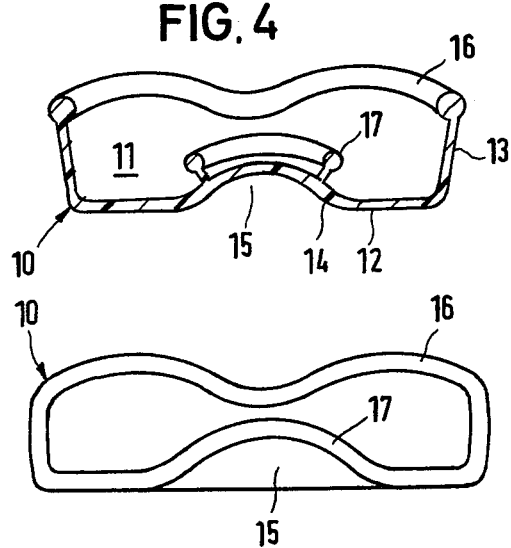
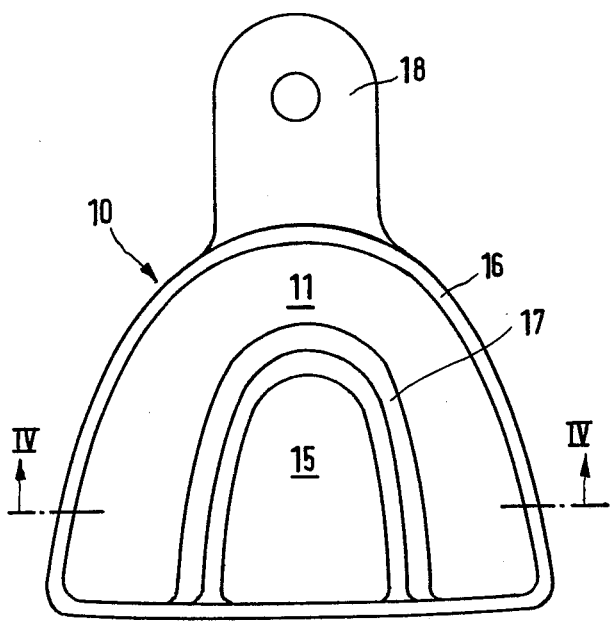
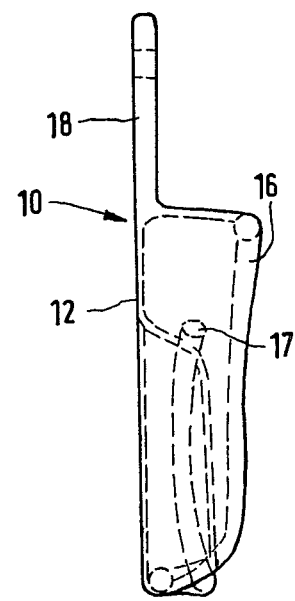

APPLIANCE FOR TAKING DENTAL IMPRESSIONS AND METHOD AND APPARATUS FOR MAKING THE SAME

BACKGROUND OF THE INVENTION

The present invention relates to an impression appliance for dental purposes, in which a reception channel for dental impression materials is adapted to the shape of the human jaw and is horseshoe-shaped. This channel is bounded on one side by a base plate and along its inner and outer edge by sections turning upward from the base plate plane in the same direction. These sections are provided on the channel inside with retention edges that are away from the base plate and have undercuts in the area of the open channel side; the invention also relates to a method for manufacturing such impression appliances, and to a tool for implementing this method.

Impression appliances are used for making impressions of teeth and gums. The impression is a negative reproduction of the teeth or gums. It is made by filling the reception channel of an impression appliance with plastic hardening material, placing the appliance in the patient's mouth and pressing it against the upper or lower jaw of the patient so that the teeth or gums are fully reproduced in the plastic material as a negative. After the dental impression material has hardened, the impression appliance with the material in its reception channel is withdrawn from the teeth or the gums, retaining the negative reproduction of the teeth or gums.

By pouring plaster of Paris into these impressions, true models of the teeth and gums are obtained. Such models are used in dentistry for diagnostic, jaw-orthopedic and prothesis purposes.

Impression appliances should ensure that, on the one hand, the plastic impression material during contact with the teeth or gums forms an exact reproduction of the latter, and, on the other hand, that this reproduction is preserved when the appliance is removed from the mouth of a patient, i.e., that the reproduction does not become deformed or detaches from the appliance. This requiremnet is satisfied only inadequately by the appliances known up to now.

To improve the adherence of the impression material to the appliance, it has been proposed that the walls of the reception cavity or channel for the impression material be provided with perforations. This measure ensures that, during removal of the impression from the patient's mouth, damage to the impression is avoided. However, it has been found difficult to obtain good impressions with such perforated walls in the area of the reception channel for the impression material, because upon applying impression material, the contact pressure is reduced by the perforations in the appliance.

Impression appliances whose reception cavities for the impression material are confined by closed walls do not have this drawback. However, with such appliances, while removing an impression from a patient's mouth, the impression easily detaches, and undesirable and frequently unnoticed changes of the impressions occur.

Since even non-perforated impression appliances have been found unsatisfactory, it has also been suggested that along the inside edges of the reception cavities, which mostly form U-shaped channels, there be soldered to the appliance partitions, so-called retention edges in the form of peripheral wires. Such impression appliances will meet practical requirements as long as the soldered retention edges are intact. However, it has been found that the soldered retention edges easily detach, especially when removing a hardened impression from such an appliance. As a result, these rather expensive appliances frequently become useless after a brief period of use.

In view of the inadequacies prevailing in the state of the art, it is the object of the present invention to provide an impression appliance as initially described, which equally ensures an exact reproduction of the teeth or gums, and the preservation of this reproduction during removal of such impression from a patient's mouth. In addition, the impression appliance to be provided is to have much durability, and must be economical to produce.

Accordingly, another object of the present invention is to provide a process for manufacturing such impression appliances and a tool suitable for implementing the process.

SUMMARY OF THE INVENTION

The objects of the present invention are achieved by providing an impression appliance which comprises a one-piece plastic molded part with retention edges directly molded from sections rising from the plane of the base plate. A handgrip extends outward from the base plate on the closed side of the horseshoe shape, and the handgrip is an integral part of the appliance.

In place of the previously known appliances, produced by drawing or as sheet metal parts with the handgrip soldered on, and the wires soldered as retention edges in the area of the inside lengthwise edges of the partitions bounding the reception channel for the dental impression material, the present invention uses a one-piece plastic shaped part. The manufacture of such an appliance from plastic proceeds in accordance with an improvement of the present invention in that the shaped parts in an already known manner, are molded in a two-piece mold joined along a mating surface and are molded in a still warm and partially plastic condition, with brief elastic deformation of the areas provided with or adjacent to undercuts. In this manner, many designs meeting the requirements of the retention edges can be realized.

Another improvement of the present invention is the tool for manufacturing impression appliances from plastic by the aforementioned process through an extrusion die design which comprises two tool sections joined along a mating surface. A cavity corresponding to the impression appliance is formed between them. The mating surface between these tool sections follows the course of the retention edge. This extends along the turned-up sections bounding the reception channel on the outside at a distance from the base plate. The undercut regions of the impression appliance correspond to that section of the one tool component which projects appreciably beyond the mating surface. Such a tool may, to great advantage, be provided with a solid core which projects beyond the mating surface of the tool and is provided with recesses corresponding to the retention edges of the impression appliance; knock-out pins, which act in the area of the impression appliance base plate, extend through this core. It is advantageous to locate the solid core on the closing side of the tool.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWING

FIG. 1 is a plan view and shows an upper jaw impression appliance with the open side of the reception channel facing upward;

FIG. 2 shows a side view of the impression appliance of FIG. 1;

FIG. 3 shows a front view of the impression appliance;

FIG. 4 shows a section taken along line IV—IV in FIG. 1;

FIG. 5 shows possible cross-sectional shapes of the retention edges;

DESCRIPTION OF THE PREFERRED EMBODIMENTS

Figure 9:
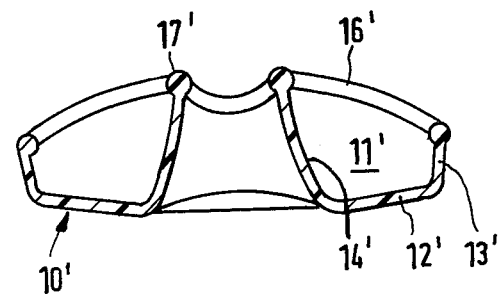
FIGS. 6 through 9 show a lower jaw impression appliance, with the views similar to FIGS. 1 through 4.
Figure 8:
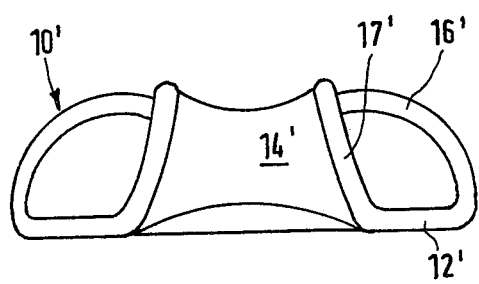
Figure 6:
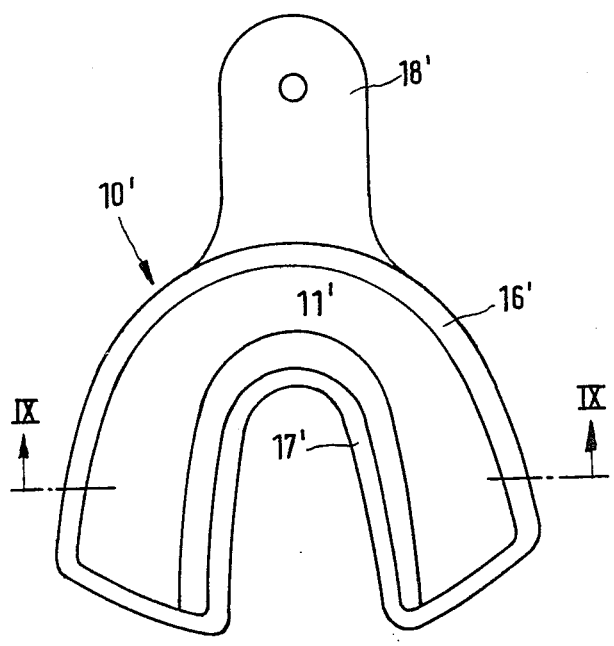
Figure 7:
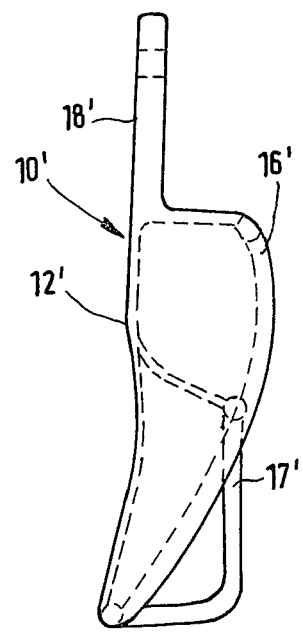

The impression appliance, denoted by 10 in FIG. 1, has a reception channel 11 whose shape is adapted to the shape of the human maxilla and whose top view is nearly horseshoe-shaped. This reception channel is bounded by a base plate 12 and adjacent arclike sections 13, 14. The sections 13, 14 bounding the reception channel 11 extend from the base plate in the same direction. While section 13 forms a peripheral rim flange including the horseshoe shape, the internal boundary of reception channel 11 is part 15 of base plate 12 which is turned upward in the central region of the horseshoe. At a distance from the base plate, the sections 13, 14 bounding reception channel 11 are provided on the channel inside with peripheral retention edges 16, 17. At the closed side of the horseshoe, a handgrip 18 in the form of a flat lug projects from base plate 12.

Characteristic of the impression appliance is its one-piece construction and its manufacture from synthetic material. Accordingly, the handgrip 18 is part of the base plate and the retention edges are formed as part of the sections 13, 14 which bound the reception channel 11.

Possible shapes of the retention edges are shown in corss section in FIG. 5. The cross section 20 corresponds with the cross sectional shapes of retention edges 16, 17, which shapes were used with the above-described upper jaw impression appliance. Alternative cross sections are illustrated by 21 and 22, without, however, exhausting the possibilities of other shapes.

For the lower jaw impression appliance, illustrated in FIGS. 6 through 9, the same reference numerals are used for similar parts as in FIGS. 1 through 4, but with an apostrophe (') for distinction.

This impression appliance 10' also has a reception channel 11' whose shape is adapted to the shape of the human mandible and whose top view is nearly horseshoe shaped. This reception channel is bounded by flange-like sections 13', 14' which extend from base plate 12'. In contrast with the spoon-shape of FIG. 1, the center sections between the legs of the horseshoe is cut out. The flange-like sections 13', 14' are again provided on the channel inside at the edges removed from the base plate with peripheral retention edges 16', 17'. Furthermore, corresponding to the maxilla impression appliance, a one-piece handgrip 18' projects from base plate 12'.

Figure 10:
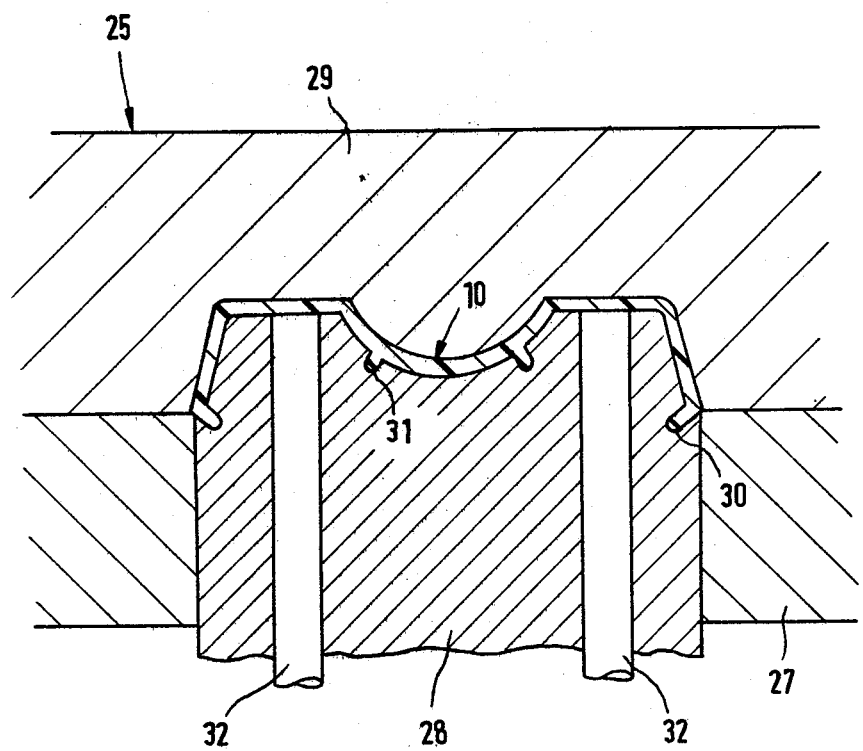
FIG. 10 shows a tool and a sectional view of an impression appliance held in a die mold; the section runs approximately along section line IV—IV in FIG. 1.

The tool shown in FIG. 10 is cross section taken through line IV—IV in FIG. 1 is a die mold comprising two sections joining along a mating surface 26 (not shown). The bottom section of the tool comprises a plate 27 with a core 28 accommodated in a plate recess. This core extends upwards beyond the mating surface 26 and its shape conforms to the contour of the maxilla impression appliance. The matching contour of the impression appliance is reproduced in the upper section 29 of the tool. When the tool sections 27, 29 are joined at the mating surface 26, there is formed between the plunger 28, which is an integral part of the tool bottom section, and the recess in the upper part 29, a hollow cavity corresponding to the impression appliance. The plunger 28 extends beyond the mating surface by the height of the flange-like section 13 which surrounds the reception channel 11 on the outside. Along the mating surface which follows the course of the retention edges on the flange-like sections bounding the reception channel of the appliance on the outside, peripheral grooves 30, corresponding to the shape of the retention edges, protrude into the core. In the area of the central arc between the legs of the horseshoe-shaped reception channel, peripheral grooves 31 are provided in the core. Similar to the retention edges with the finished impression appliance, grooves 30, 31 have undercuts or back tapers. Knock-out pins 32, which can be moved vertically, extend through the core 28 which is an integral part of bottom section 27.

Die molds of the aforementioned type are already known in the art. Therefore, their function and their design need not be described in detail here. It is pointed out, however, that with the upper section 29 removed from the bottom section 27, the forming of the molded parts takes place in the not fully hardened warm state; the knock-out pins 32 acting on the channel inside the area of the workpiece base plate are pushed upward; the undercut parts of the workpiece undergo a brief deformation; and after ejection from the tool, they return to their molded shape.

Without further analysis, the foregoing will so fully reveal the gist of the present invention that others can, by applying current knowledge readily adapt it for various applications without omitting features that, from the standpoint of prior art, fairly constitute essential characteristics of the generic or specific aspects of this invention, and therefore, such adaptations should and are intended to be comprehended within the meaning and range of equivalence of the following claims.

We claim:

1. A dental impression appliance comprising: a one-piece molded part of synthetic material with a form-stable reception channel for impression material, said reception channel being horseshoe-shaped to correspond to a human jaw, a handgrip extending from the closed side of the horseshoe outward, a base plate with a plane in which the handgrip extends, said reception channel being bounded on one side by said plane, said reception channel being bounded along its inside and outside edges by sections raised towards the same side from the plane of said base plate, said sections having retention edges on the inside of said channel forming undercuts running at a distance from the base plate in the area of the open side of the channel.

2. A dental impression appliance as defined in claim 1 wherein said one-piece molded part of synthetic material with formstable reception channel is free of wire mesh screen means.

* * * * *